(12) United States Patent
Feroldi et al.

(10) Patent No.: US 11,963,663 B2
(45) Date of Patent: Apr. 23, 2024

(54) FIBER ENDOSCOPE

(71) Applicant: Stichting VU, Amsterdam (NL)

(72) Inventors: Fabio Feroldi, Amsterdam (NL); Johannes Fitzgerald De Boer, Amsterdam (NL)

(73) Assignee: Stichting VU, Amsterdam (NL)

(*) Notice: Subject to any disclaimer, the term of this patent is extended or adjusted under 35 U.S.C. 154(b) by 878 days.

(21) Appl. No.: 17/042,488

(22) PCT Filed: Mar. 28, 2019

(86) PCT No.: PCT/NL2019/050193
§ 371 (c)(1),
(2) Date: Sep. 28, 2020

(87) PCT Pub. No.: WO2019/190321
PCT Pub. Date: Oct. 3, 2019

(65) Prior Publication Data
US 2021/0022590 A1 Jan. 28, 2021

(30) Foreign Application Priority Data
Mar. 29, 2018 (NL) ..................................... 2020692

(51) Int. Cl.
*A61B 1/00* (2006.01)
*A61B 5/00* (2006.01)
*G02B 6/28* (2006.01)

(52) U.S. Cl.
CPC ........ *A61B 1/00167* (2013.01); *A61B 1/0017* (2013.01); *A61B 5/0062* (2013.01); *A61B 5/0084* (2013.01); *G02B 6/2821* (2013.01)

(58) Field of Classification Search
CPC .............. G02B 6/02042; G02B 6/3624; A61B 5/0062; A61B 5/0084; A61B 5/0082;
(Continued)

(56) References Cited

U.S. PATENT DOCUMENTS 4,976,265 A * 12/1990 Falcial ................. A61B 5/4211
600/343
8,861,910 B2 * 10/2014 Yun ....................... G02B 6/2835
385/43

(Continued)

FOREIGN PATENT DOCUMENTS

CN 102980658 A * 3/2013
CN 209712839 U * 12/2019 ......... A61B 1/00009
(Continued)

OTHER PUBLICATIONS

CN-209712839-U translation (Year: 2019).*
(Continued)

*Primary Examiner* — Michelle R Connelly
*Assistant Examiner* — Mary A El-Shammaa
(74) *Attorney, Agent, or Firm* — Banner & Witcoff, Ltd.

(57) ABSTRACT

A fibre endoscope system (100) comprises a catheter (10) with a probe head (10a) for entering into a body cavity (C) adjacent or near a sample region (S). A source fiber (11) has a first fiber ending (11a) and a signal fiber (12) has a second fiber ending (12a) both remote from the probe head (10a) but separate. A sampling fiber (13) has a third fiber ending (13a) disposed at the probe head (10a). A fiber coupler (15) is configured to optically couple at least the source fiber (11) to the sampling fiber (13), and the sampling fiber (13) to the signal fiber (12). A sampling fiber length (L13) of the sampling fiber (13) between a fiber coupler (15) and the third fiber ending (13a) is shorter than a source fiber length (L11) of the source fiber (11) between the fiber coupler (15) and the first fiber ending (11a).

14 Claims, 4 Drawing Sheets

(58) Field of Classification Search
CPC . A61B 1/0082; A61B 1/0017; A61B 1/00167; A61B 1/005; A61B 1/00064; A61B 1/00071; A61B 1/00096; A61B 1/00097; A61B 1/00105; A61B 1/00013; A61B 1/00002; A61B 1/00009; A61B 1/313

See application file for complete search history.

(56) References Cited

U.S. PATENT DOCUMENTS

| | | | |
|---|---|---|---|
| 9,332,942 B2 * | 5/2016 | Jaffer | G01N 21/4795 |
| 2010/0106025 A1 | 4/2010 | Sarfaty et al. | |
| 2012/0093461 A1 * | 4/2012 | Ramachandran | G02F 1/3513 |
| | | | 385/28 |
| 2016/0374562 A1 * | 12/2016 | Vertikov | A61B 5/0095 |
| | | | 600/424 |
| 2019/0212761 A1 * | 7/2019 | Swanson | A61B 5/0075 |

FOREIGN PATENT DOCUMENTS

| | | | | |
|---|---|---|---|---|
| WO | WO-9939630 A1 * | 8/1999 | | A61B 5/14535 |
| WO | WO-2019144195 A1 * | 8/2019 | | G01J 3/0218 |
| WO | WO-2020113570 A1 * | 6/2020 | | A61B 1/00009 |

OTHER PUBLICATIONS

CN-102980658-A translation (Year: 2013).*
Wendy-Julie Madore et al., "Asymmetric double-clad fiber couplers for endoscopy," Optics Letters, Optical Society of America, Nov. 1, 2013, vol. 38, No. 21, pp. 4514-4517.
Jul. 4, 2019, International Search Report and Written Opinion, PCT/NL2019/050193.

* cited by examiner

FIBER ENDOSCOPE

CROSS-REFERENCE TO RELATED APPLICATIONS

This application is a U.S. National Stage application under 35 U.S.C. § 371 of International Application PCT/NL2019/050193 (published as WO 2019/190321 A1), filed Mar. 28, 2019, which claims the benefit of priority to Application NL 2020692, filed Mar. 29, 2018. Benefit of the filing date of these prior applications is hereby claimed. Each of these prior applications is hereby incorporated by reference in its entirety.

TECHNICAL FIELD AND BACKGROUND

The present disclosure relates to a fiber endoscope for imaging or otherwise measuring sampling regions inside the body.

Molecular imaging has the potential to provide functional information about the physiological properties of a living organism. For example, the origin of the signal can be exogenous such as in immunofluorescence where a contrast agent such as a fluorophore is used, that can be conjugated to a ligand that targets a specific cell receptor or protein. Accordingly, the aim can be to specifically detect a particular biomolecular target in a cell and/or on a cell surface and/or outside the cell (extracellular matrix). The contrast can also be endogenous, for example in Raman spectroscopy, non-linear microscopy, and lifetime fluorescence imaging. Typically, these techniques may rely on the detection of very weak signals compared to the intensity of the excitation light used to create the contrast.

Measurement system may include bulky light delivery and collection systems and scanners, for example a microscope. However, to access remote locations, such as the internal organs of the human body, there is a need to use smaller devices such as imaging catheters or endoscopes. Optical fibers can be used to bridge the distance between the light source/imaging sensor and the probe head of the endoscope system. In this way, the probe head disposed at the sampling region location can be relatively compact. A particularly convenient configuration for light delivery and collection is the double-clad fiber (DCF), which is a fiber comprising two concentric waveguides. Typically, the excitation light travels through a (smaller) inner core while the larger cladding collects the weak emitted signal, for improved collection efficiency and separation of signals. Further advantages of this design may include its low cost, and the possibility of using double-clad fiber couplers. These are passive optical elements composed of two fused optical fibers that are able to extract the collected signals efficiently. For example Madore et al. [Optics Letters Vol. 38, No. 21, Nov. 1, 2013] describe asymmetric double-clad fiber couplers for endoscopy.

Unfortunately, the known optical fiber configurations for endoscopy may suffer from undesired background signals. So there remains a need for an improved fiber endoscope where problems of the prior art can be alleviated while at least some of their advantages can be maintained.

SUMMARY

The inventors find that optical fibers may exhibit undesired effects when light is guided through them. For example, these effects may include native fluorescence and Raman scattering background signals generated in the fiber. Despite the weakness of these background signals compared to the excitation light, their intensity can be on the same order of magnitude as the signal to be detected, e.g. fluorescence. So, the effects may significantly decrease the signal-to-noise ratio of the measurement, to the point that the noise (caused by the background signal of the fiber itself) could overwhelm the desired signal. In addition to single mode fibers, also multi-clad fiber configurations, e.g. DCF fiber configurations, may exhibit significant noise when light is coupled through its core. The noise may even be higher since background signals generated in the fiber core can be captured in the cladding e.g. due to the typically higher numeric aperture of the clad mode. To better understand the source of the undesired effects, the inventors have performed experiments such as illustrated in FIG. 1B which show that the magnitude of background noise may increase with the length of the fibers, more particularly the length of the fiber through which the (high intensity) source light travels.

These and other insights have led to new designs in fiber endoscopy in which the length of the (concentric) fibers carrying both the source illumination to the sample region and the collected light back from the sample region is kept as short as possible. For instance this can be achieved by placing a (double-clad) fiber coupler inside the catheter close to the distal end, as close as possible to the area of interest such as the tissue, or by placing the DCF coupler as close as possible to a scanning mechanism such as a set of galvos. The source light path can e.g. be separate from the signal light path for most of the distance between the probe head and the measurement console. In this way, noise created by the excitation light in the inner core bleeding into the cladding can be minimized.

Some configurations may be suitable for point-measurements which is popular e.g. for Raman spectroscopy. In other or further designs, where scanning is desired, placing the double-clad fiber coupler inside the catheter may rely on a scanning mechanism. However, if the DCF would rotate as part of the scanning mechanism, separate fibers connecting to the probe head could intertwine when connected to a stationary measurement console. To resolve this, the scan mechanism can also be inside the catheter, and all kinds of distally scanned catheters, where a micro-motor or a piezo-element is used to scan the beam at the point-of-interest could be used (for example in cardiovascular molecular imaging, and in brain esophageal, lung and bladder cancer molecular imaging). To further improve the usability of the catheter, it is found desirable to use flexible double-clad fiber couplers to decrease the allowed bending radius of the endoscope.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1A:
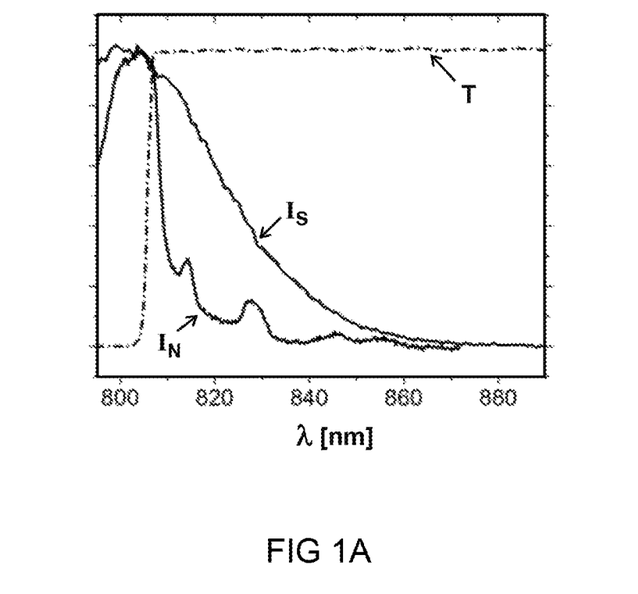
FIGS. 1A and 1B illustrate experiments to determine noise contribution of the fiber itself.
Figure 1B:
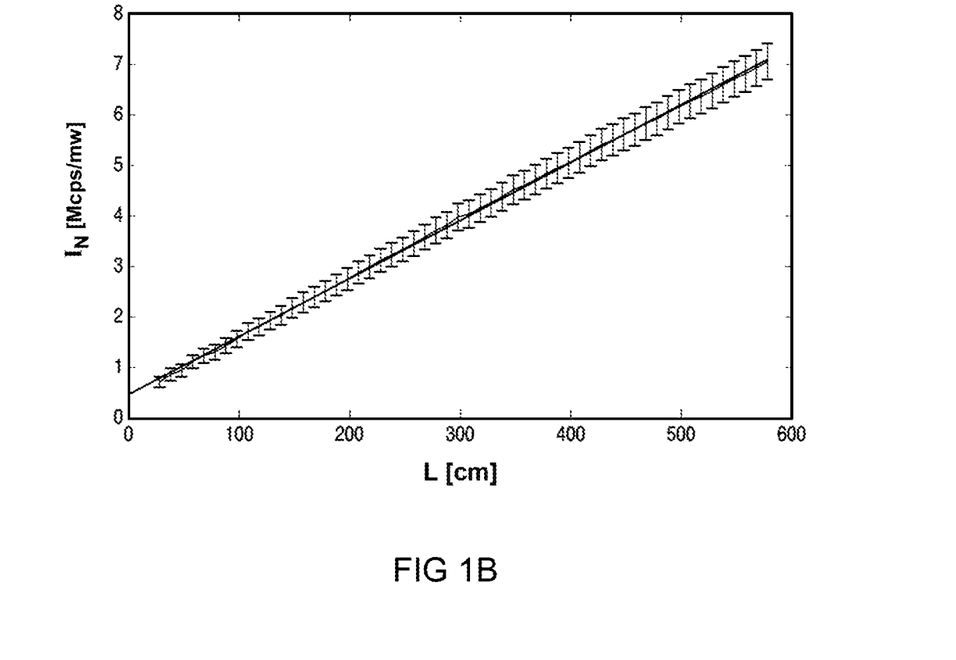

FIG. 1A illustrates an example of (normalized) spectral intensities of a signal "$I_S$" and background noise "$I_N$" measured using a passive double-clad fiber. In the experiment, near infrared source light at 780 nm travels through the single-mode core of the fiber to illuminate a sample, and the resulting (fluorescence) signal "$I_S$" travels back through the inner cladding of the fiber surrounding the core. To filter the relative high intensity source light, a long-pass wavelength filter with transmission "T" as indicated can be used, e.g. passing only light above 800 nm and/or a bandpass filter, passing only a band of light in the signal spectral region. However, this filter may not be able to block all noise "$I_N$", e.g. attributed to Raman scattering of the source light. Its magnitude may in some cases be comparable to the signal, e.g. fluorescence collected from the sample and can therefore severely affect the signal to noise ratio.

FIG. 1B illustrates experimental results wherein the relative noise contribution "$I_N$" (million counts per second per milliwatt of source light) is measured as a function of the fiber length "L" (centimeter) of a double-clad fiber. It will be noted that the relative noise "$I_N$" increases with the length "L" of the fiber. From a linear fit it may be noted that there can be a small offset, e.g. due to a residual Raman scattering component in the DCF coupler. In any case, it will be appreciated that the source light induced noise in the fiber may be minimized by keeping the fiber as short as possible. However, it is still desired to reach remote locations such as inside the body, e.g. wherein the light may travel several meters from the light source to the sample.

Without being bound by theory, sources of noise such as Raman radiation induced by source light in the core of the fiber, may scatter isotropically, allowing the large-NA cladding of the fiber to collect it and guide it back to the detector. So it will be appreciated that the influence of noise generated by the source light in the fiber core may alleviated if the part of the cladding through which the signal can travel back to the detector is kept as short as possible, while the total length of fiber through which the source light travels separately from the signal may have less effect. These and other insights can lead to further improvements in fiber based imaging, e.g. as described herein.

Figure 2A:
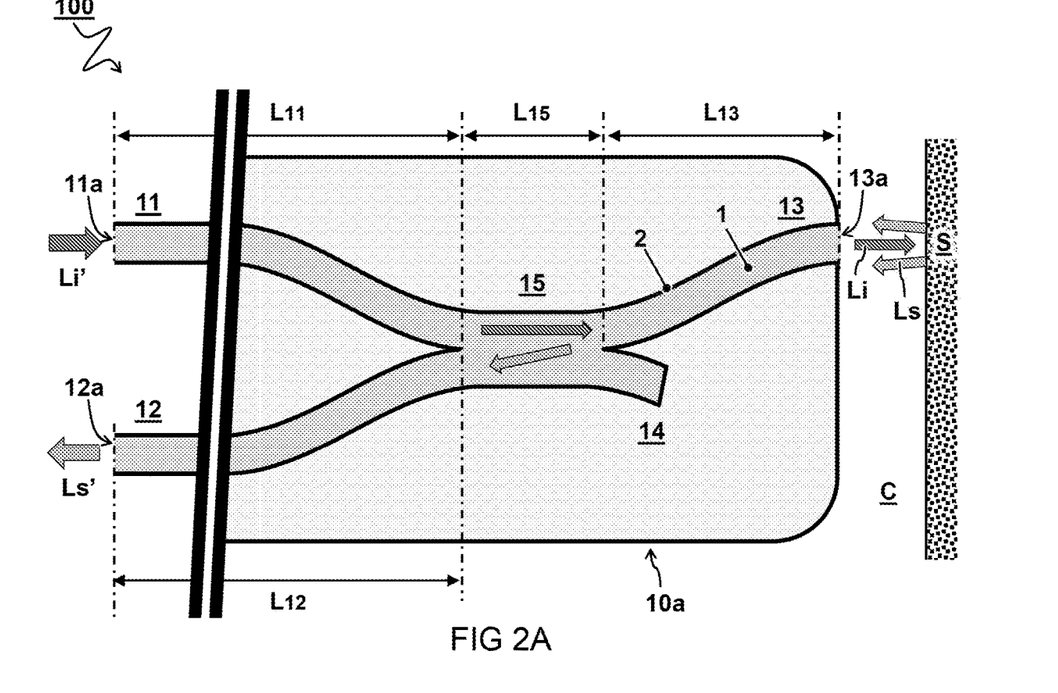
FIGS. 2A and 2B illustrate schematic cross-section views of an embodiment of a fibre endoscope system.
Figure 2B:
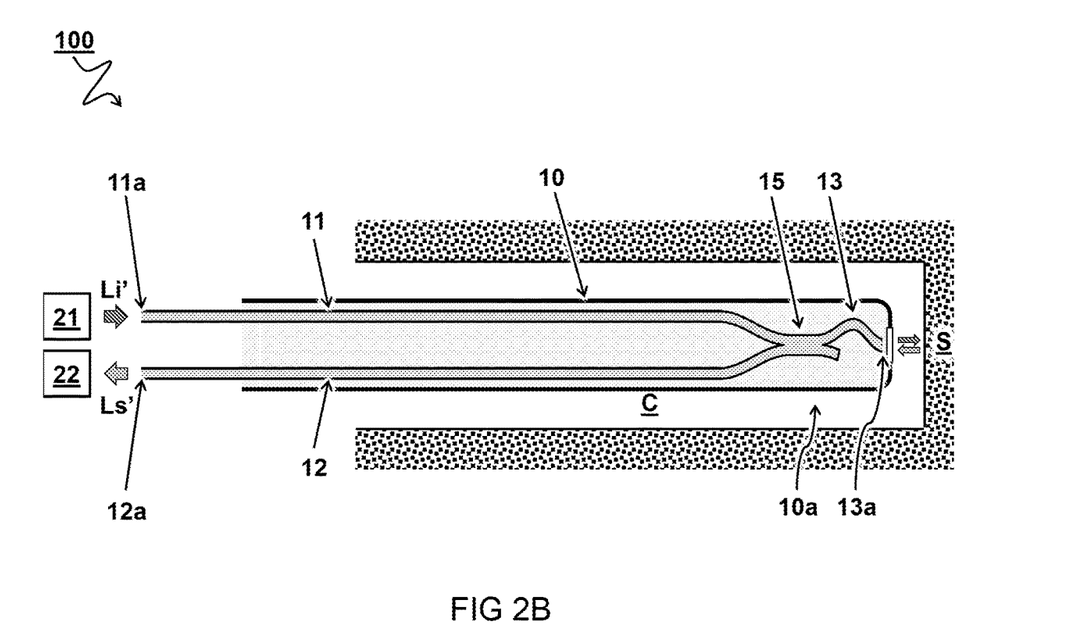

FIGS. 2A and 2B illustrate one embodiment of a fibre endoscope system 100. The system comprises an (imaging) catheter 10 with a probe head 10a for entering into a body cavity, duct, or vessel "C" adjacent or near a sample region S to be measured. This may include artificially created openings, such as cavities or ducts to guide surgery, e.g. brain surgery where the skull is partially removed and the endoscope inserted. The system comprises a source fiber 11 with a first fiber ending 11a remote from the probe head 10a. The system comprises a signal fiber 12 with a second fiber ending 12a also remote from the probe head 10a but separate from the source fiber 11. The remoteness or variable position of the fiber endings with respect to the probe head 10a is indicated by the double black bars in FIG. 2A. The system comprises a sampling fiber 13 with a third fiber ending 13a disposed at the probe head 10a. The system also comprises a fiber coupler 15 forming a connection between at least the fibers 11,12,13, and possibly a residual fiber 14 which may be blocked. In the embodiment of FIGS. 2A and 2B, the fibers are single cladded with a fiber core 1 and a first fiber cladding 2 surrounding the fiber core 1. For example, the single cladded fiber may be a single-mode, preferably multi-mode fiber.

Figure 3A:
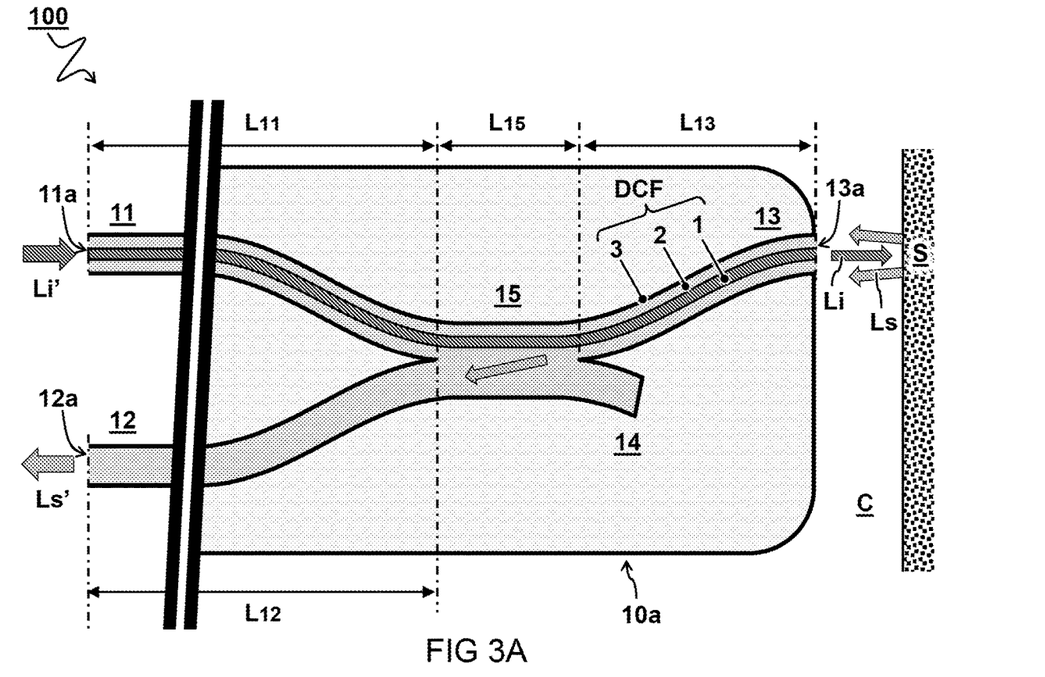
FIGS. 3A and 3B illustrate schematic cross-section views of another embodiment.
Figure 3B:
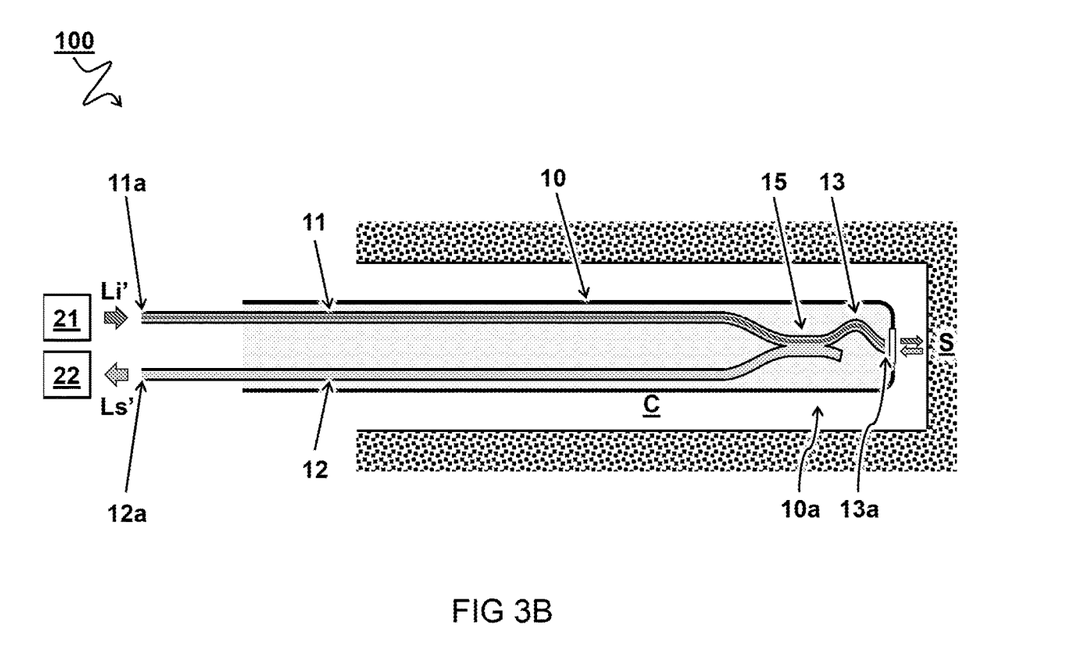

FIGS. 3A and 3B illustrate a more preferred embodiment, wherein the sampling fiber 13 is a multi-clad fiber. Typically, the multi-clad fiber comprises at least a fiber core 1 with a first fiber cladding 2 around the fiber core 1, and a second fiber cladding 3 surrounding the first fiber cladding 2. Optionally, further cladding layers may be added (not shown). For example, two, three, four or more cladding layers can be used to vary a diameter or cross-section area of the transmitting and/or receiving surface at the fiber ending. In some embodiments, particularly with a multi-clad fiber, the fiber coupler 15 may be configured to optically couple the source fiber 11 to the fiber core 1 of the sampling fiber 13. In other or further embodiments, the fiber coupler 15 may be configured to couple the first fiber cladding 2 of the sampling fiber 13 to the signal fiber 12.

With reference to either embodiments, most preferably a sampling fiber length L13 of the sampling fiber 13 between the fiber coupler 15 and the third fiber ending 13a is shorter than a source fiber length L11 of the source fiber 11 between the fiber coupler 15 and the first fiber ending 11a. For example, the sampling fiber length L13 is less than the source fiber length L11 (or the signal fiber length L12) by at least a factor two, three, five, ten, fifty, hundred, or more. For example, the sampling fiber length L13 is less than thirty centimeters, preferably less than ten centimeters, less than five centimeters, less than three centimeters, less than one centimeter, or even less, e.g. on the order of one or more millimeter. The shorter the sampling fiber length, e.g. compared to the source fiber length or in absolute terms, the less the relative noise contribution may be. Typically a total length of the fibers between the light source and the sample, in this case the source fiber length L11 plus the sampling fiber length L13, possibly including the fiber coupler length L12, is more than twenty centimeter, more than fifty centimeter, more than one meter, more than two meter, more than three meter, or even more. The longer the total length of fibers between the source and sample, the more potential benefit the present adaptations may provide in reaching remote locations for measurement.

In some embodiments, as shown in FIGS. 2B and 3B, the fibre endoscope system 100 comprises an optical interrogator configured to direct input light Li' into the first fiber ending 11a of the source fiber 11 and receive signal light Ls' from the second fiber ending 12a of the signal fiber 12. For example, the optical interrogator comprises a light source 21 for generating the input light Li', such as a laser, and a light sensor 22 for measuring the signal light Ls', e.g. photosensitive device. Also other devices (not shown), e.g. optics and electronics, may be included in the interrogator or fibre endoscope system. For example, a wavelength of the signal light Ls' may be resolved by a grating, prism, et cetera. Also optical filters such as edge filters or bandpass filters may be included, e.g. to filter out a wavelength of the input light Li' from the measured signal light Ls' and/or filter out noise wavelengths.

With continued reference to FIGS. 2A and 3A, the fiber coupler 15 is preferably configured to optically couple at least the source fiber 11 to the sampling fiber 13, and the sampling fiber 13 to the signal fiber 12. Accordingly, at least some of the input light Li' entering the first fiber ending 11a may travel through the fiber coupler 15 to exit at the third fiber ending 13a of the sampling fiber 13 as illumination light Li. Furthermore, at least some of the sample light Ls entering the third fiber ending 13a may travel through the fiber coupler 15 to exit at the second fiber ending 12a of the signal fiber 12 as signal light Ls'.

In preferred embodiments, such as shown in FIG. 3A, the fiber coupler 15 is configured to optically couple the source fiber 11 to the fiber core 1 of the sampling fiber 13. For example, the fiber core 1 of the sampling fiber 13 is configured to illuminate the sample region S with illumination light Li exiting the fiber core 1 at the third fiber ending 13a disposed at or near the probe head 10a after entering the first fiber ending 11a of the source fiber 11 as input light Li' remote from the probe head 10a.

It will be appreciated that configurations including a multi-clad fiber, such as shown in FIG. 3A, may have various advantages over configuration with only single cladded fibers, such as shown in FIG. 2A. For example, input light Li' entering the first fiber ending 11a, more particularly the fiber core of the source fiber 11, may be more efficiently coupled via the fiber core into the sampling fiber 13, e.g. avoiding the dead end of the residual fiber 14. Furthermore, an increased surface of the first fiber cladding 2 surrounding the fiber core 1 may more efficiently collect the illumination light Li from the sample region S and/or guide the light more efficiently across the fiber coupler 15 back to the signal fiber 12.

In a preferred embodiment, the multi-clad fiber, e.g. at least the sampling fiber 13, is a double-clad fiber (DCF), wherein the first fiber cladding 2 forms an inner cladding of the double-clad fiber surrounded by a second cladding 3 forming an outer cladding of the DCF. Typically, though not necessarily, the source fiber 11 and the sampling fiber 13 can both be double-clad fibers, as shown. Possibly these are formed from one original DCF or other multi-clad fiber. For example, the (original) fiber core 1 extends all the way between the first fiber ending 11a and the third fiber ending 13a to deliver the illumination light Li. Typically, transmission losses through the fiber core can be less than ten percent, preferably less than five percent. In an alternative embodiment (not shown) the sampling fiber 13 can be a DCF while the source fiber 11 can be a single clad fiber comprising only the fiber core and e.g. one outer cladding.

In some embodiments with a multi-clad fiber, the fiber coupler 15 is configured to optically couple the first fiber cladding 2 of the sampling fiber 13 to the signal fiber 12. For example, the first fiber cladding 2 of the sampling fiber 13 is configured to collect sample light Ls from the illuminated sample region S and transmit at least some of the collected sample light Ls via the fiber coupler 15 into the signal fiber 12 to exit the signal fiber 12 as signal light Ls'. Preferably, the first fiber cladding 2 has a diameter that much greater than the fiber core 1, e.g. greater by a factor of more than two, three, five, ten, or more. Accordingly, an entry surface area of the first fiber cladding 2 at the third fiber ending 13a of the sampling fiber 13 for collecting the sample light Ls can be much greater than an exit surface area of the fiber core 1 at the third fiber ending 13a for delivering the illumination light Li. In this way, more sample light may be collected.

In some preferred embodiments with a multi-clad fiber, the fiber core 1 forms a single-mode fiber while the first fiber cladding 2 may form a multi-mode fiber. In some embodiments, the fiber coupler 15 is formed by fusing a double-clad fiber to a single fiber, e.g. multimode fiber, to produce an asymmetric multi-clad fiber (e.g. DCF) coupler as shown, or another multi-clad fiber (not shown). Typically, the (multimode) inner cladding transfer for such a coupler can be fifty percent, or more, e.g. at least sixty percent or at least seventy percent. In alternative embodiments with single fiber cladding, preferably the core is a multi-mode fiber to efficiently transmit and collect the light.

In some embodiments, the catheter 10 and/or probe head 10a has an outer diameter of less than three centimeter, less than two centimeter, less than one centimeter, less than five millimeter, less than two millimeter, or less, e.g. between 0.5-1.5 mm. Typically, the catheter 10 forms a tube around at least part of the optical fibers 11,12,13. For example, the catheter 10 comprises a medical grade material for safely entering the body. For example, the fibers have a diameter of less than one millimeter each, preferably less than half a millimeter, e.g. between ten and hundred fifty micrometer.

In a preferred embodiment, the fiber coupler 15 is disposed inside the catheter 10. Most preferably, the fiber coupler 15 is disposed in the probe head 10a of the catheter 10. For example, the probe head 10a is formed at a distal end of the catheter 10. For example, the fiber coupler 15 is less than thirty centimeter from the distal end of the catheter 10, preferably less than ten centimeter, less than five centimeters, less than three centimeters, less than one centimeter, or even less. In case the fiber coupler 15 is part of the catheter 10, preferably, it is relatively flexible. For example, the stiffness can be expressed in terms of the flexural modulus e.g. according to a three point bending test as explained where a guidewire of >10 GPa is considered relatively stiff. Preferably, the fiber coupler as described herein is more flexible, e.g. with a flexural rigidity less than ten GPa, less than one GPa less than hundred Mega Pascal (MPa), less than ten MPa, or less.

Figure 4A:
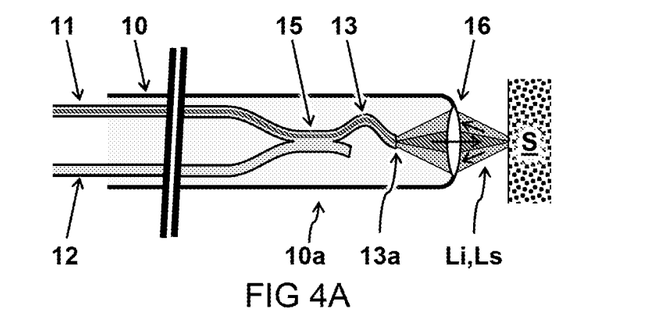
FIGS. 4A-4D illustrate further embodiments.
Figure 4B:
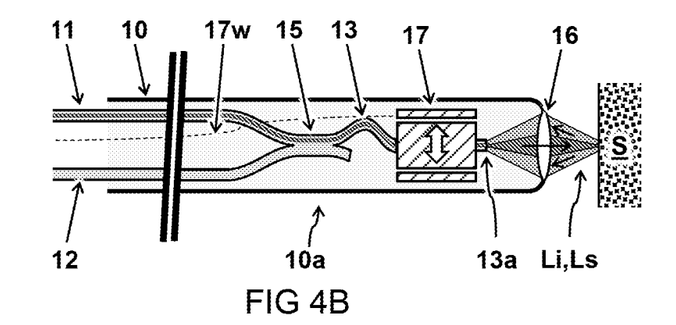

FIGS. 4A-4B illustrate further aspects of example probe heads 10a in embodiments of the fibre endoscope system. While the figures show preferably multi-clad fiber configurations such as FIG. 3B, in principle also single-clad fibers may be used such as FIG. 2B.

In some embodiments, as shown, the probe head 10a includes a focusing optics 16 configured to focus illumination light Li from the third fiber ending 13a of the sampling fiber 13, e.g. the fiber core, onto the sample region S and/or collecting sample light Ls from the sample region S back onto the third fiber ending 13a, e.g. the first fiber cladding.

In some embodiments, e.g. according to FIG. 4A, the focusing optics 16 comprises a lens forming a front light exit port of the probe head 10a. While a traditional lens is shown, alternatively or additionally a gradient index lens (GRIN) is used. Instead of the lens forming the exit port, the lens can also be disposed elsewhere, e.g. inside the probe head 10a. For example, the exit port can be simply formed by a transparent material of the probe head 10a. Also other types of focusing optics 16 can be used such as curved mirrors, or the focusing optics 16 can be omitted for some applications. While the embodiment shows light exiting a front distal part of the probe head, light can also be directed to the side of the probe head.

Figure 4C:
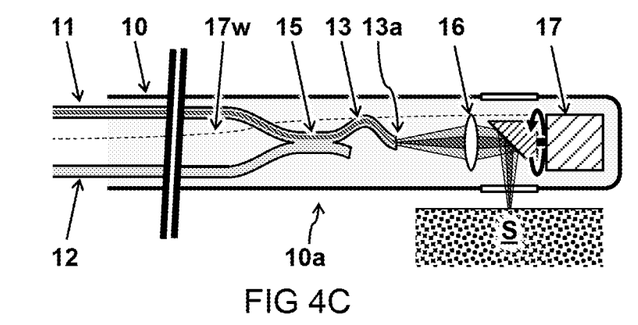
Figure 4D:
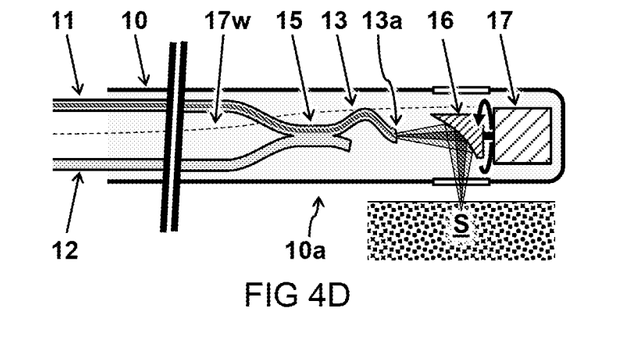

In some preferred embodiments, the probe head 10a includes an actuator 17 configured to vary the position of the illuminated spot on the sample region S, e.g. with a reciprocating, rotating, or other periodic motion. In some embodiments, e.g. according to FIG. 4B, the third fiber ending 13a of the sampling fiber 13 itself is moved, e.g. in a reciprocating motion using a piezo actuator integrated into the probe head 10a. In another or further embodiment, the light beam is redirected between the third fiber ending 13a and the sample region S, e.g. in a rotating or reciprocating motion using a micro-motor with rotating mirror or other beam redirection means integrated into the probe head, e.g. according to FIG. 4C or 4D. To externally control and/or power the actuator 17, electrical wiring 17w may be included inside the catheter 10 together with the optical fibers. Alternatively, control can be automatic and/or a local power source such as battery may be used. In some embodiments, an optically-driven motor is used, e.g. wherein the cladding may act as a source or conduit of radiation for a photovoltaic cell powering the motor. Also externally driven motors, e.g. with varying magnetic fields, can be envisaged. The focusing optics 16 may be separate from the actuator 17, as shown in FIGS. 4B and 4C, or they can be integrated, as shown in FIG. 4D. For example, the actuator 17 may rotate a curved mirror to sweep an area of the sample region S around the probe head 10a.

For the purpose of clarity and a concise description, features are described herein as part of the same or separate embodiments, however, it will be appreciated that the scope of the invention may include embodiments having combinations of all or some of the features described. For example, while embodiments were shown for various features included in the probe head of an imaging catheter, also alternative components may be envisaged by those skilled in the art having the benefit of the present disclosure for achieving a similar function and result. E.g. optical, mechanical, and/or electrical components may be combined or split up into one or more alternative components. The various elements of the embodiments as discussed and shown offer certain advantages, such as compact and reliable design. Of course, it is to be appreciated that any one of the above embodiments or processes may be combined with one or more other embodiments or processes to provide even further improvements in finding and matching designs and advantages. It is appreciated that this disclosure offers particular advantages to endoscopy, e.g. fluorescence measurement, and in general can be applied for minimizing noise in optical fibers particularly with concentric fiber ending.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

The invention claimed is:

1. A fibre endoscope system comprising
a catheter with a probe head for entering into a body cavity, duct, or vessel adjacent a sample region to be measured;
a source fiber with a first fiber ending remote from the probe head;
a signal fiber with a second fiber ending also remote from the probe head but separate from the source fiber;
a sampling fiber with a third fiber ending disposed at the probe head; and
a fiber coupler disposed inside the probe head at a distal end of the catheter and configured to optically couple at least
the source fiber to the sampling fiber, and
the sampling fiber to the signal fiber;
wherein a sampling fiber length of the sampling fiber between the fiber coupler and the third fiber ending is shorter than a source fiber length of the source fiber between the fiber coupler and the first fiber ending by at least a factor two.

2. The system according to claim 1, wherein the sampling fiber is a multi-clad fiber comprising at least a fiber core with a first fiber cladding around the fiber core, and a second fiber cladding surrounding the first fiber cladding; wherein the fiber coupler is configured to optically couple at least
the source fiber to the fiber core of the sampling fiber, and
the first fiber cladding of the sampling fiber to the signal fiber.

3. The system according to claim 1, wherein the sampling fiber length is less than five centimeter and the source fiber length is more than one meter.

4. The system according to claim 1, wherein the fiber coupler is relatively flexible with a flexural rigidity less than one Giga Pascal.

5. The system according to claim 1, wherein the fibre endoscope system comprises an optical interrogator configured to direct input light into the first fiber ending of the source fiber and receive signal light from the second fiber ending of the signal fiber.

6. The system according to claim 1, wherein the sampling fiber is a double-clad fiber, wherein the first fiber cladding forms an inner cladding of the double-clad fiber surrounded by a second fiber cladding forming an outer cladding of the double-clad fiber.

7. The system according to claim 1, wherein the fiber coupler is an asymmetric multi-clad fiber coupler, wherein a fiber core extends through the coupler between the source fiber and the sampling fiber.

8. The system according to claim 1, wherein a fiber core of the sampling fiber is configured to illuminate the sample region with illumination light exiting the fiber core at the third fiber ending disposed at the probe head after entering the first fiber ending of the source fiber as input light remote from the probe head.

9. The system according to claim 1, wherein a first fiber cladding of the sampling fiber is configured to collect sample light from the illuminated sample region and transmit at least some of the collected sample light via the fiber coupler into the signal fiber to exit the signal fiber as signal light.

10. The system according to claim 1, wherein the probe head includes a focusing optics configured to focus illumination light from the third fiber ending of the sampling fiber onto the sample region and/or collecting sample light from the sample region back onto the third fiber ending.

11. The system according to claim 1, wherein an actuator is integrated into the probe head and configured to vary the position of a illuminated spot on the sample region with a reciprocating or rotating motion.

12. The system according to claim 1, wherein a light beam is redirected between the third fiber ending and the sample region, in a rotating or reciprocating motion using a micromotor with rotating mirror or other beam redirection means integrated into the probe head.

13. The system according to claim 1, wherein the probe head includes an actuator configured to move a focusing optics to redirect and focus a light beam from the third fiber endings onto the sample region.

14. The system according to claim 1, wherein the third fiber endings of the sampling fiber itself is moved by an actuator integrated into the probe head.

* * * * *